United States Patent [19]

Lesins

[11] Patent Number: 5,145,971
[45] Date of Patent: Sep. 8, 1992

[54] PROCESS FOR THE PREPARATION OF OXYDIPHTHALIC ACID AND PURIFIED OXYDIPHTHALIC ANHYDRIDE FROM CRUDE OXYDIPHTHALIC ANHYDRIDE

[75] Inventor: Viesturs Lesins, Buffalo, N.Y.

[73] Assignee: Occidental Chemical Corporation, Niagara Falls, N.Y.

[21] Appl. No.: 783,026

[22] Filed: Oct. 25, 1991

[51] Int. Cl.⁵ ................. C07D 307/89; C07D 307/77
[52] U.S. Cl. ................................ 549/250; 549/236; 549/239; 549/241; 549/247
[58] Field of Search ............... 549/236, 239, 241, 247, 549/250

[56] References Cited

U.S. PATENT DOCUMENTS

| | | | |
|---|---|---|---|
| 1,301,388 | 4/1919 | Conover et al. | 549/250 |
| 2,786,805 | 3/1957 | Sullivan et al. | 549/250 |
| 3,338,923 | 8/1967 | Peterlein | 549/239 |
| 3,540,987 | 11/1970 | Garkisch et al. | 549/250 |
| 3,650,906 | 3/1972 | Gehsken et al. | 549/250 |
| 3,850,967 | 11/1974 | Suatoni | 549/250 |
| 3,869,479 | 3/1975 | Barth et al. | 549/250 |
| 4,215,051 | 7/1980 | Schroeder et al. | 549/250 |
| 4,906,760 | 3/1990 | Mueller et al. | 549/250 |
| 4,914,231 | 4/1990 | Manami et al. | 562/429 |
| 4,948,921 | 8/1990 | Green et al. | 562/413 |

FOREIGN PATENT DOCUMENTS

| | | | |
|---|---|---|---|
| 3339392 | 5/1985 | Fed. Rep. of Germany | 549/250 |
| 9199683 | 11/1984 | Japan | 549/250 |
| 160176 | 1/1964 | U.S.S.R. | 549/250 |

*Primary Examiner*—Cecilia Tsang
*Attorney, Agent, or Firm*—Richard D. Fuerle

[57] ABSTRACT

A process for the preparation of purified oxydiphthalic acid from impure oxydiphthalic anhydride, by treating with a mixture of water and propionic acid or butyric acid to produce oxydiphthalic acid. The acid may be treated to reform oxydiphthalic anhydride. The most effective composition range for the acid-water mixture is from about 25% acid to 75% acid.

13 Claims, No Drawings

PROCESS FOR THE PREPARATION OF OXYDIPHTHALIC ACID AND PURIFIED OXYDIPHTHALIC ANHYDRIDE FROM CRUDE OXYDIPHTHALIC ANHYDRIDE

BACKGROUND OF THE INVENTION

This invention relates to a method for converting oxydiphthalic anhydride into purified oxydiphthalic acid. The oxydiphthalic acid may be used as a curing agent for epoxy resins, and may be converted into its esters which are useful as plasticizers. In addition, the purified oxydiphthalic acid may be converted into oxydiphthalic anhydride, which is purer than the oxydiphthalic anhydride starting material. Oxydiphthalic anhydride is useful in the production of polyimide resins. Such polyimide resins have a variety of uses, but are often used in electronic application. For electronic use, it is desirable to have oxydiphthalic anhydride of high purity and low ionic concentration.

Oxydiphthalic anhydride is often prepared from 4-chlorophthalic anhydride by coupling two molecules of the 4-chlorophthalic anhydride to form oxydiphthalic anhydride. The crude product of such a coupling reaction often includes organic solvents, unreacted starting material and catalysts, ionic substances, and various colored materials of unknown composition. The process of the present invention is useful for the conversion of oxydiphthalic anhydride prepared by the coupling of two molecules of 4-chlorophthalic anhydride into pure oxydiphthalic acid. However, the process is general and may be used to convert impure oxydiphthalic anhydride from any source into pure oxydiphthalic acid. The process is particularly useful in preparing oxydiphthalic acid which is converted into oxydiphthalic anhydride for use in the production of polyimides for electronic use.

Graebe has disclosed in Leibigs Annalen der Chemie Vol. 149, p. 18, 1869, that tetrachlorophthalic acid may be purified by recrystallization from water followed by sublimation. During the sublimation process the acid is converted to the anhydride which may be reconverted to the acid by boiling in water.

U S. Pat. No. 1,301,388 discloses that phthalic anhydride may be purified by dissolving in non-aqueous solvent, and passing the solution through a material, capable of absorbing colored impurities, such as charcoal. The solution is filtered and passed through a series of crystallization tanks of successively lower temperatures. Pure phthalic anhydride is obtained in the crystallization tanks maintained at the highest temperature and the impurities are crystallized at lower temperatures.

U. S. Pat. No. 2,786,805 discloses that phthalic anhydride may be purified by mixing sufficient water with the anhydride to form a slurry, heating the slurry to 375°–400° F., removing the anhydride from the slurry by passing steam into the mixture and condensing the vapors at 300° F. whereby a condensate of phthalic anhydride is produced which is substantially free of water. The phthalic anhydride is then further purified by fractional distillation.

U.S. Pat. No. 2,937,189 discloses that pyromellitic acid, in water solution, may be treated with activated carbon to remove any organic impurities which may be present and treated with a metal extracting agent, e.g., a cation exchange resin to remove any metals which may be present.

U.S. Pat. No. 2,985,665 discloses that phthalic anhydride may be purified by passing molten phthalic anhydride over an activated carbon bed.

U.S. Pat. No. 3,236,885 discloses that pyromellitic acid may be purified by dissolving the acid in water, treating the aqueous solution with activated carbon, separating the carbon from the aqueous solution and recovering the purified pyromellitic acid from the water.

U.S. Pat. No. 3,338,923 discloses a method of purifying pyromellitic dianhydride by treating the impure dianhydride with ketones. The patent also discloses that it is known in the prior art that pyromellitic dianhydride may be purified by converting the dianhydride into the acid with water and recrystallizing the acid from water in the presence of activated carbon.

U.S. Pat. No. 4,870,194 discloses that oxydiphthalic anhydride can be purified by filtering or centrifuging a hot solution of oxydiphthalic anhydride in a high boiling solvent to remove impurities, followed by cooling the solution to precipitate the oxydiphthalic anhydride, which can be removed from the solution by filtration or centrifuging.

U.S. Pat. No. 4,906,760 discloses that metal ion impurities may be removed from aromatic anhydrides "by refluxing the anhydride in an aqueous solution to decyclize the anhydride and to ionize or dissolve the metal impurities in the water vehicle, provide an activated adsorption agent such as activated carbon to clarify the solution, filtering off the absorption agent (and recovering the polyacid therefrom by washing the filter cake with warm water for return to the main solution) allowing the solution to stand and cool and precipitate the purified polyacid, filtering and washing the polyacid and finally recyclizing the polyacid back to the purified anhydride."

British Patent 823,507, as abstracted in CA 54:7655C, discloses that tetrachlorophthalic acid may be purified by dissolving the acid in a water solution containing 2–20% of a water miscible ether such as dioxane, tetrahydofuran and acetals. The crude tetrachlorophthalic anhydride is dissolved in a mixture of water and the ether and filtered hot. Upon cooling to room temperature, the crystals of acid form which are then washed and dried to form tetrachlorophthalic anhydride.

U.S. Pat. No. 4,914,231 discloses a method for purifying diphenylsulfone tetracarboxylic acids by dissolving the crude tetracarboxylic acid in a mixture of water and acetic acid and allowing the acid to crystallize in order to obtain a highly purified diphenylsulfone tetracarboxylic acid. The concentration of acetic acid in the solvent mixture ranges from 2 to 90 volume % and preferably from about 10 to about 70 volume %. When the crude diphenylsulfone tetracarboxylic acid contains a heavy metal ion, removal of the heavy metal ion is more effective if the solution is treated with a cation exchange resin, or with oxalic acid prior to crystallization. The Examples show that if cation exchange resins or oxalic acid are not used, the heavy metal ion level is not reduced below about 100 ppm. The amount of the solvent mixtures relative to the crude diphenyl sulfone is about 1 to 200 times and preferably 3 to 50 times.

European Patent Number 0 421 046 A1 discloses a process for producing highly pure 3,3',4,4'-biphenyl tetra-carboxylic acid or the dianhydride thereof. The 3,3',4,4'-biphenyltetracarboxylic acid is heated at a temperature of 160° to 260° C. in order to drive off certain impurities. In this portion of the process, the acid is cyclized to the anhydride. The anhydride is then treated with hot water at a temperature of 95° to 105° C. In this portion of the process, certain impurities dissolve in the water and the anhydride is converted to the acid. If the anhydride is the desired product, it may be reformed by heating the tetraacid.

SUMMARY OF THE INVENTION

It has been discovered that crude oxydiphthalic anhydride may be treated with a mixture of water and propionic acid or butyric acid to form purified oxydiphthalic acid. The most effective composition range for the water-acid mixture is from about 25% acid to 75% acid. After treatment with the water-acid mixture, the resulting oxydiphthalic acid may be cyclized to form oxydiphthalic anhydride.

DETAILED DESCRIPTION OF THE INVENTION

According to the process of the present invention, crude oxydiphthalic anhydride is treated with an aqueous solution of either propionic or butyric acid. This treatment produces oxydiphthalic acid which is substantially purer than the crude oxydiphthalic anhydride from which it is prepared. The present process removes organic solvents, unreacted starting materials and catalysts, ionic substances, and various colored materials of unknown composition. If desired, the oxydiphthalic acid produced may be dehydrated (cyclized) to form oxydiphthalic anhydride which is substantially purer than the crude oxydiphthalic anhydride starting material. Thus, the process may be used as a method of converting crude oxydiphthalic anhydride into purified oxydiphthalic acid. Alternatively, with the addition of an optional dehydration step, the process may be used as a method of purifying oxydiphthalic anhydride.

Surprisingly, mixtures of water and either propionic or butyric acid function better, in applicant's process, than mixtures with either acetic or formic acids. Propionic acid is the preferred acid for use in the present invention. While butyric acid provides good results, its use is not preferred because of its well-known odor. The oxydiphthalic acid produced by the present process leads, after cyclization, to a purer grade of oxydiphthalic anhydride. Thus, the process may be used to produce a purified grade of oxydiphthalic acid or oxydiphthalic anhydride.

We have found that the color-forming potential of various samples of oxydiphthalic anhydride may be compared by preparing solutions of standard concentration and comparing the percent transmittance at 430 nm. A percent transmittance of 80 or above, at 430 nm, is considered highly desirable. While treatment with propionic acid solutions regularly produces, after cyclization, material with a percent transmittance of 80 or above, acetic acid solutions generally produce materials with a percent transmittance of less than 80.

It has been found that propionic acid and water treatment is effective for reducing the level of ionic impurities in the oxydiphthalic acid produced. The present process produces, after the optional cyclization step, an oxydiphthalic anhydride in which the concentration of individual metal ions is one part per million or less. In fact, the copper level is reduced to 0.1 ppm or less. Even phosphorus, which is difficult to remove, is reduced to a level of 8.5 ppm or less (see Example 5). This result is surprising in view of U.S. Pat. No. 4,914,231, which demonstrates that when diphenyl sulfone tetracarboxylic acid was dissolved in acetic acid and water solutions the concentration of ionic materials in the final product could not be reduced below approximately 100 ppm unless the solution was treated with a cation exchange resin or a chelating agent.

The process of the present invention is not a classical recrystallization. In a classical recrystallization method the material to be purified is dissolved in a solvent, often at an elevated temperature, and the solution is filtered. After filtration, the filtrate is cooled, or concentrated, and the purified material crystallizes out of the solution. On the other hand, the present process begins with a slurry of crude oxydiphthalic anhydride in an aqueous solvent. As the mixture is heated, the entire slurry may dissolve, to form a solution which may remain clear for a brief period. The formation of a clear solution is unpredictable. At low ratios of oxydiphthalic anhydride to the aqueous phase, a clear solution is more likely to form than is the case at high ratios. Although I do not wish to be bound by theory, it is possible that a supersaturated solution of oxydiphthalic acid may form. Crystallization of the oxydiphthalic acid in such a solution would occur fairly quickly. However, such a solution might occasionally remain clear for a brief period. Whatever the reasons may be for the occasional appearance of a clear solution, a filtration cannot reliably be done in the present process. A clear solution may not form, and if it does form, it is not likely to remain clear for a sufficient period of time to accomplish a filtration.

The mixture of oxydiphthalic anhydride in the aqueous phase is warmed to a temperature of between about 40° C. and the reflux temperature, at atmospheric pressure, of the aqueous solvent. At the lower temperatures in the range, the hydrolysis of the oxydiphthalic anhydride to the oxydiphthalic acid is somewhat slow, and the process takes longer. Whatever temperature is selected, the mixture is held at that temperature until the anhydride is substantially hydrolyzed. In practice, the mixture is held for a longer period of time in order to assure that the hydrolysis is, in fact, complete.

When establishing a reaction time for a given temperature, it is possible to determine the completeness of hydrolysis by several methods. If the crude oxydiphthalic anhydride has a significant level of colored impurities, the crystals within the slurry will appear white when hydrolysis is complete. Alternatively, samples may be withdrawn from the slurry and dried. Upon heating, the oxydiphthalic acid will dehydrate to form the anhydride. Each molecule of oxydiphthalic acid produces two molecules of water upon dehydration to oxydiphthalic anhydride. The gasses formed on heating may be conducted to a Karl Fischer titration apparatus to determine the amount of water formed. The amount of water formed indicates how much acid is present. Comparison to the weight of the sample reveals if any oxydiphthalic anhydride remains. Other methods for determining the amount of oxydiphthalic anhydride present, such as chromatography, will be readily apparent to those skilled in the art. The hydrolysis is substantially complete when the quantities of oxydiphthalic anhydride remaining are negligible.

Except for a possible brief period of total dissolution, the present process is conducted with a slurry rather than with a solution. Accordingly, there is no opportunity in the present process for hot filtration of the solution of the product to be purified. Since the process does not involve a step of hot filtration of a solution of the oxydiphthalic acid, there is no possibility for using adsorption agents within the process. Thus, if one were to add a material such as silica gel, or activated carbon, it could not be removed by filtration and would show up in the final product.

It is surprising that the process of the present invention removes colored materials without the use of adsorption agents such as charcoal. The fact that adsorption agents are not required by the present process is a major advantage since the initial cost of the charcoal is saved and the process does not produce a charcoal waste stream which must either be purified and recycled or disposed of as a waste. In addition, a filtration step for removal of the adsorption agent is not required.

There is an optimum range of acid content for the aqueous solution used for treatment of the crude oxydiphthalic anhydride. Aqueous mixtures of the appropriate concentration provide better purification than is provided by a solvent mixture containing either more of the carboxylic acid or less than the optimum range. We have found that the preferred range of composition of the aqueous mixture is 25 to 75 weight percent acid in water. The most preferred concentration range based on color improvement for the solvent is about 40–60% by weight acid in water.

The process may be conducted at rather high loading of oxydiphthalic anhydride to the aqueous phase. The loading is defined as the weight fraction of oxydiphthalic anhydride in the mixture. A loading of oxydiphthalic anhydride is typically in the range of 25 to 40%. When more solvent is used, such that the loading of oxydiphthalic anhydride is typically less than 20%, the process provides a pure product. However, such operation is not desirable since it can result in the loss of product remaining in the large volume of solvent. In addition, the large volumes of aqueous phase would add to the cost of the process. The lowest practical limit for conducting the process would probably be a loading of oxydiphthalic anhydride of approximately 10%. On the other hand, at loadings of oxydiphthalic anhydride of greater than about 35%, the mixture becomes increasingly thick and difficult to process. In addition, at a loading of about 35% and above, the color improvement may not be as great as that obtained at lower loadings. Those skilled in the art will readily be able to select a loading which produces the degree of color improvement and ease of handling which is desired.

After the mixture has been heated for sufficient time to assure that the oxydiphthalic anhydride has been substantially hydrolyzed to the oxydiphthalic acid, the liquid and solid phases are separated. The separation may be accomplished by any of the methods known by those skilled in the art, such as filtration or centrifuging. Once the solid phase has been separated, it may then be washed. A washing step is optional, especially when large quantities of solvent compared to the amount of oxydiphthalic acid are used. However, the use of a wash is definitely preferred because it helps to remove the solvent from the oxydiphthalic acid and thereby lessens the chance for accidental re-introduction of impurities into the acid. Either a water wash or a wash consisting of a propionic acid and water mixture may be used. The wash solution may vary in composition from pure water to approximately 75% by weight propionic acid in water. If an acid wash is chosen, the preferred range is 25 to 75% propionic acid. It is preferred to use a cold wash solution in order to avoid the loss of the oxydiphthalic acid which could dissolve in the wash solution. We have found that somewhat better color properties are obtained if a mixture of propionic acid and water is used as a washing solution.

Optionally, the oxydiphthalic acid may be recyclized (dehydrated) to form oxydiphthalic anhydride. There are many methods of accomplishing recyclization which are well-known to those skilled in the art. For example, one method is treatment of the oxydiphthalic acid with acetic anhydride. In this method, the acetic anhydride is converted to acetic acid and the oxydiphthalic acid is converted to the anhydride. Other chemical reagents have been used to remove the water to reform the anhydride. The oxydiphthalic acid may be treated with a hot, high boiling solvent in which water is immiscible. The water formed by recyclization distills out along with the solvent, is separated from the solvent, and thereby removed from the process. The oxydiphthalic acid may be melted and cooled. In the process, oxydiphthalic anhydride if formed. A convenient method of cyclization which has been used is to heat the oxydiphthalic acid in a dryer at a temperature of 200°–220° C. for several hours in order to remove the water and form the dianhydride. Since the process of purification works equally well with any method of cyclization of the dianhydride, a person skilled in the art may readily select a cyclization method which best fits his needs.

EXAMPLES

EXAMPLE 1

To 12.5 g of oven-dried oxydiphthalic anhydride (ODPA), were added 37.5 g of the acid-water mixture. The resulting slurry was heated to reflux and held at reflux for approximately one hour. The mixture was cooled to room temperature over night and filtered. The solid material was washed with 50 g of cold water. The oxydiphthalic acid was dried for 20 to 24 hours at a temperature of between 200° and 220° C. The resulting ODPA was weighed to determine the yield and the color of the product was measured by determining the % transmittance at a wavelength of 430 nm. The results are summarized in the following chart.

| Solvent | Yield (%) | Color (% T) at 430 nm |
| --- | --- | --- |
| Propionic acid (27%)/water (48%) | 89 | 81 |
| Butyric acid (27%)/water (48%) | 81 | 86 |

EXAMPLE 2

Using a procedure similar to that for Example 1, a mixture containing various ratios of propionic acid to water was used. Samples of ODPA weighing approximately 30 g were mixed with the acid-water mixture. The samples contained various percentages of dichlorobenzene (DCB) as an example of the type of residual organic solvents which could exist in crude samples of ODPA. The mixtures of ODPA and the aqueous solution had the weight fraction composition set forth in the table below. After reflux, the mixture was cooled for 3 to 4 hours before the solid and liquid phases were separated by filtration. The solid was washed with 50 g of cold water. The results of these experiments are shown in the following chart.

| | | Weight Fraction | | | Color |
|---|---|---|---|---|---|
| ODPA | DCB | Propionic Acid | Water | Yield % | % T at 430 nm |
| 0.250 | 0.075 | 0.675 | 0.000 | 95.7 | 47.4 |
| 0.250 | 0.038 | 0.712 | 0.000 | 93.7 | 47.1 |
| 0.250 | 0.000 | 0.750 | 0.000 | 96.3 | 47.2 |
| 0.250 | 0.074 | 0.338 | 0.338 | 88.0 | 84.0 |
| 0.250 | 0.000 | 0.375 | 0.375 | 89.0 | 82.2 |
| 0.250 | 0.038 | 0.356 | 0.356 | 88.3 | 83.6 |
| 0.250 | 0.075 | 0.000 | 0.675 | 96.5 | 48.6 |
| 0.250 | 0.038 | 0.000 | 0.712 | 96.7 | 50.4 |
| 0.250 | 0.000 | 0.000 | 0.750 | 96.7 | 50.6 |

It is apparent that both pure propionic acid and pure water produce samples with lower transmittance at 430 nm. The best results are produced by treatment with an aqueous mixture containing approximately equal portions by weight of propionic acid and water.

EXAMPLE 3

Using a procedure similar to that for Example 1, mixtures containing various ratios of propionic acid to water were used. Samples of ODPA weighing approximately 20–25 g were mixed with the aqueous solution. The samples contained various percentages of dichlorobenzene (DCB). The mixtures of ODPA and the aqueous solvent had the weight fraction composition set forth in the table below. After reflux, the mixture was cooled for 3 to 4 hours before the solid phase was separated from the liquid phase by filtration. The solid was washed with 50 g of cold water. The results of these experiments are shown in the following chart.

| | | Weight Fraction | | | Color |
|---|---|---|---|---|---|
| ODPA | DCB | Propionic Acid | Water | Yield % | % T at 430 nm |
| 0.350 | 0.075 | 0.457 | 0.118 | 96.4 | 56.8 |
| 0.350 | 0.021 | 0.378 | 0.251 | 94.1 | 79.6 |
| 0.350 | 0.080 | 0.342 | 0.228 | 93.6 | 83.2 |
| 0.350 | 0.035 | 0.321 | 0.294 | 92.7 | 78.4 |
| 0.350 | 0.095 | 0.289 | 0.266 | 93.6 | 85.6 |
| 0.350 | 0.074 | 0.288 | 0.288 | 93.9 | 87.2 |
| 0.350 | 0.000 | 0.325 | 0.325 | 92.8 | 84.0 |
| 0.350 | 0.090 | 0.280 | 0.280 | 92.8 | 83.6 |
| 0.350 | 0.080 | 0.228 | 0.342 | 93.6 | 81.2 |
| 0.350 | 0.021 | 0.251 | 0.378 | 92.7 | 82.6 |
| 0.350 | 0.077 | 0.115 | 0.458 | 95.6 | 64.6 |

EXAMPLE 4

Using a procedure similar to that for Example 1, mixtures containing various ratios of propionic acid to water were used. Samples of ODPA weighing approximately 25 g were mixed with the aqueous solution. The samples contained various percentages of dichlorobenzene (DCB). The mixtures of ODPA and the aqueous solvent had the weight fraction composition set forth in the table below. After reflux, the mixture was cooled for 3 to 4 hours before the solid phase was separated from the liquid phase by filtration. The solid washed with 30 g of cold water. The results of these experiments are shown in the following chart.

| | | Weight Fraction | | | Color |
|---|---|---|---|---|---|
| ODPA | DCB | Propionic Acid | Water | Yield % | % T at 430 nm |
| 0.300 | 0.129 | 0.381 | 0.190 | 94.0 | 70.0 |
| 0.300 | 0.053 | 0.216 | 0.431 | 92.8 | 76.2 |
| 0.300 | 0.245 | 0.303 | 0.152 | 94.4 | 70.9 |
| 0.300 | 0.245 | 0.253 | 0.202 | 93.2 | 84.8 |
| 0.300 | 0.052 | 0.324 | 0.324 | 91.2 | 82.1 |
| 0.300 | 0.128 | 0.286 | 0.286 | 92.0 | 85.2 |
| 0.300 | 0.246 | 0.227 | 0.227 | 94.4 | 84.2 |
| 0.300 | 0.053 | 0.303 | 0.344 | 92.4 | 78.0 |
| 0.300 | 0.129 | 0.262 | 0.309 | 92.8 | 82.8 |
| 0.300 | 0.245 | 0.202 | 0.253 | 94.8 | 82.5 |
| 0.300 | 0.053 | 0.239 | 0.408 | 92.5 | 78.1 |
| 0.300 | 0.129 | 0.201 | 0.370 | 93.4 | 75.4 |
| 0.300 | 0.245 | 0.152 | 0.303 | 94.8 | 76.8 |
| 0.300 | 0.053 | 0.216 | 0.431 | 86.8 | 83.0 |
| 0.300 | 0.129 | 0.190 | 0.381 | 93.2 | 77.2 |

EXAMPLE 5

To 125 mL Erlenmeyer flask equipped with a condenser, a fluorocarbon coated stir bar, and a hot plate/magnetic stirrer, was charged nominally 20 g of ODPA and 80 g of 50% propionic acid in water. The resulting mixture was heated to reflux and refluxed for 2 hours. The resulting slurry was then cooled to room temperature over the course of 5½ hours at which time the slurry was vacuum filtered to recover the solids. The resulting filter cake was then washed with deionized water. A second purification was done, identical to the first, except that the wash solution was a 50% propionic acid in water solution. In each case the resulting filter cake was then placed in a 200°–220° C. oven for approximately 16 hours. The heat treatment recyclized the oxydiphthalic acid to oxydiphthalic anhydride. Each batch of anhydride was analyzed for ionic impurities, and for all ions tested, the level of impurities was at or below the detection limit of the analytical method. The results are shown in the table below.

| ELEMENT | CRUDE ODPA (ppm) | PURIFIED ODPA (water wash) (ppm) | PURIFIED ODPA (50% propionic acid wash) (ppm) |
|---|---|---|---|
| Cu | 0.1877 | ≦0.1 | ≦0.1 |
| Ca | 1.415 | ≦0.5 | ≦0.5 |
| Fe | 0.7269 | ≦0.5 | ≦0.5 |
| K | 34 | ≦0.5 | 0.5 |
| Na | 2.8 | ≦0.5 | ≦0.5 |
| Ni | 9.956 | ≦1.0 | ≦1.0 |
| P | 45.42 | ≦8.5 | ≦8.5 |
| Zn | 1.162 | ≦0.5 | ≦0.5 |
| YIELD | | 85% | 84% |
| COLOR (% T @ 430 nm) | | 78.6 | 82.8 |
| ODPA CHARGE | | 19.99 g | 20.41 g |
| 50% PROPIONIC ACID CHARGE | | 80.16 g | 79.14 g |
| WASH CHARGE | | 41.5 g | 39.7 g |

COMPARATIVE EXAMPLE 1

To 12.5 g of oven-dried oxydiphthalic anhydride (ODPA), were added 37.5 g of acetic acid water mixture. The resulting slurry was heated to reflux and held at reflux for approximately one hour. The mixture was cooled to room temperature over night and filtered. The solid material was washed with 50 g of cold water.

The oxydiphthalic acid was dried for 20 to 24 hours at a temperature of between 200° and 220° C. The resulting ODPA was weighed to determine the yield and the color of the product was measured by determining the % transmittance at a wavelength of 430 nm. The results are summarized in the following chart.

| Solvent | Yield (%) | Color (% T) |
|---|---|---|
| Acetic acid (48%)/water (27%) | 93 | 77 |

COMPARATIVE EXAMPLE 2

Using a procedure similar to that for Example 1, mixtures containing various ratios of acetic acid to water were used. Samples of ODPA weighing approximately 35 g were mixed with the aqueous solution. The mixtures of ODPA and the aqueous solvent had the weight fraction composition set forth in the table below. After reflux, the mixture was cooled for 3 to 4 hours before the liquid phase was separated from the solid phase by filtration. The solid was washed with 50 g of cold water. The samples contained various percentages of dichlorobenzene (DCB). The results of these experiments are shown in the following chart.

| ODPA | DCB | Acetic Acid | Water | Yield % | Color % T |
|---|---|---|---|---|---|
| 0.250 | 0.000 | 0.750 | 0.000 | 94.2 | 47.0 |
| 0.250 | 0.038 | 0.712 | 0.000 | 93.1 | 44.0 |
| 0.250 | 0.075 | 0.675 | 0.000 | 92.6 | 49.4 |
| 0.250 | 0.000 | 0.375 | 0.375 | 93.4 | 75.6 |
| 0.250 | 0.038 | 0.356 | 0.356 | 92.9 | 72.8 |
| 0.250 | 0.074 | 0.338 | 0.338 | 93.7 | 74.0 |
| 0.250 | 0.075 | 0.000 | 0.675 | 96.0 | 51.0 |
| 0.250 | 0.038 | 0.000 | 0.712 | 94.6 | 51.2 |
| 0.250 | 0.000 | 0.000 | 0.750 | 95.4 | 51.4 |

I claim:

1. A process for the production of purified oxydiphthalic acid from impure oxydiphthalic anhydride comprising the steps of
   1) mixing the impure oxydiphthalic anhydride with an aqueous solvent containing 25-75 wt % of a carboxylic acid selected from the group consisting of propionic acid and butyric acid to form a mixture;
   2) warming said mixture until the ODPA has been substantially hydrolyzed to oxydiphthalic acid;
   3) cooling said mixture; and
   4) separating the solid oxydiphthalic acid from the aqueous phase.

2. A process according to claim 1 with the additional step of cyclizing the oxydiphthalic acid to form oxydiphthalic anhydride in purified form.

3. A process according to claim 2 with the additional step of washing the oxydiphthalic acid, which has been separated from the aqueous phase, with water containing between 0 and 75% by weight of an acid selected from the group consisting of propionic acid and butyric acid.

4. A process according to claim 3 in which the carboxylic acid is propionic acid.

5. A process according to claim 4 conducted at 40° C.

6. A process according to claim 4 conducted at 75° C.

7. A process according to claim 4 conducted at the reflux temperature of the solvent.

8. A process according to claim 7 in which the cyclization step is conducted by heating the oxydiphthalic acid to a temperature between 200° and 220° C.

9. A process according to claim 2 in which the carboxylic acid is butyric acid.

10. A process according to claim 9 conducted at 50° C.

11. A process according to claim 9 conducted at 75° C.

12. A process according to claim 9 conducted at the reflux temperature of the solvent.

13. A process according to claim 12 in which the cyclization step is conducted by heating the oxydiphthalic acid to a temperature between 200° and 220° C.

* * * * *